US 12,385,050 B1

United States Patent
Masmoudi et al.

(10) Patent No.: US 12,385,050 B1
(45) Date of Patent: Aug. 12, 2025

(54) HEAT RESISTANT BIOPESTICIDE AND A METHOD OF PREPARING THE SAME

(71) Applicant: United Arab Emirates University, Al Ain (AE)

(72) Inventors: Khaled Masmoudi, Al Ain (AE); Mughair Abdul Aziz, Al Ain (AE)

(73) Assignee: United Arab Emirates University, Al Ain (AE)

( * ) Notice: Subject to any disclaimer, the term of this patent is extended or adjusted under 35 U.S.C. 154(b) by 0 days.

(21) Appl. No.: 18/657,159

(22) Filed: May 7, 2024

(51) Int. Cl.
| | |
|---|---|
| *C12N 15/00* | (2006.01) |
| *A01N 63/23* | (2020.01) |
| *A01N 63/50* | (2020.01) |
| *C07K 14/415* | (2006.01) |
| *C12N 15/70* | (2006.01) |

(52) U.S. Cl.
CPC ............. *C12N 15/70* (2013.01); *A01N 63/23* (2020.01); *A01N 63/50* (2020.01); *C07K 14/415* (2013.01)

(58) Field of Classification Search
CPC .................................................... C12N 15/70
See application file for complete search history.

(56) References Cited

U.S. PATENT DOCUMENTS

| | | | |
|---|---|---|---|
| 5,702,703 A * | 12/1997 | Schnepf .................. | A01N 63/50 424/93.46 |
| 7,902,334 B2 | 3/2011 | Bintrim | |

OTHER PUBLICATIONS

Jehangir (The insecticidal efficacy and performance of Bt Cotton under variable abiotic stresses—A review on recent findings. Plant Stress 8 (2023) 100151. Available online Mar. 20, 2023.*
Liu (The LEA2 gene sub-family: Characterization, evolution, and potential functions in Camellia oleifera seed development and stress response. Scientia Horticulturae, vol. 322, 2023. Available online Aug. 8, 2023.*
Zhou et al., "Overexpression of CsLEA11, a Y3SK2-type dehydrin gene from cucumber (*Cucumis sativus*), enhances tolerance to heat and cold in *Escherichia coli*,". AMB Express, 2017, vol. 7:182, 9 pages.

* cited by examiner

*Primary Examiner* — Yong D Pak
(74) *Attorney, Agent, or Firm* — Boyle Fredrickson, S.C.

(57) ABSTRACT

A biopesticide composition and a method of making the composition. The biopesticide composition comprises a biopesticide in the form of an endotoxin protein, preferably a δ-endotoxin; and a late embryogenesis abundant (LEA) protein in the form of a LEA2/dehydrin protein, wherein the ratio of endotoxin to LEA2/dehydrin proteins is 1:40. The LEA2/dehydrin proteins in the composition confers heat resistance to the endotoxin up to a temperature of about 42° C. The method of making the biopesticide composition comprises providing a biopesticide, providing a LEA protein, by isolating genes for a LEA protein from a plant and expressing the isolated gene for the LEA protein in an expression vector to produce a recombinant LEA protein, the method including combining the biopesticide and the LEA protein.

10 Claims, 6 Drawing Sheets

Specification includes a Sequence Listing.

Task 1: Identification and isolation of LEA2/dehydrin genes

Identifying and isolating the LEA2/dehydrin genes

Transformation of E. coli bacterial cells with the LEA2/dehydrin genes and plasmid extraction Confirmation of LEA2/dehydrin genes through sequencing and the presence of conserved motifs

Task 2: Cloning into the expression vector for recombinant protein production

Expression of LEA2/dehydrin proteins in the pET-28a vector

Production and purification of recombinant LEA2/dehydrin proteins

Addition of recombinant LEA2/dehydrin proteins into Bt biopesticides assay under heat stress

Task 3: In vitro characterization of recombinant LEA2/dehydrin proteins on RPW

FIG. 2

FIG. 3A        FIG. 3B        FIG. 3C
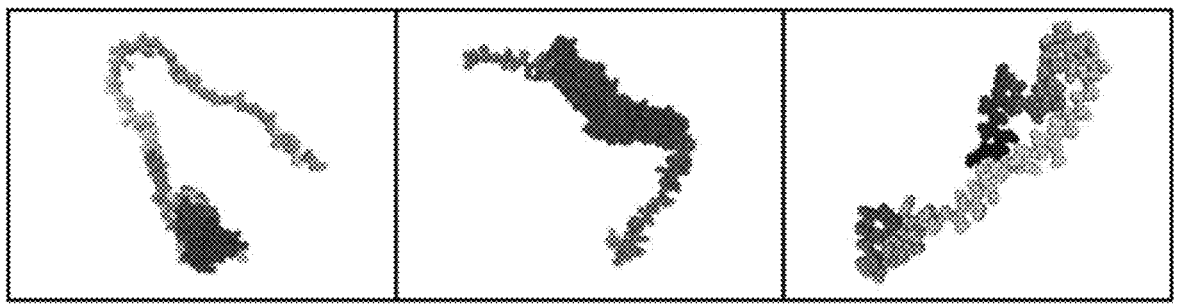
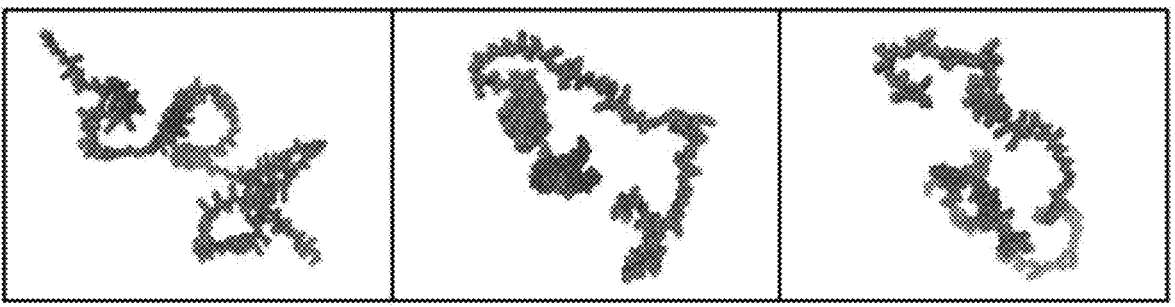
FIG. 3D        FIG. 3E        FIG. 3F

25°C

Day 5

Day 7

Day 10

42°C

Day 5

Day 7

Day 10

25°C
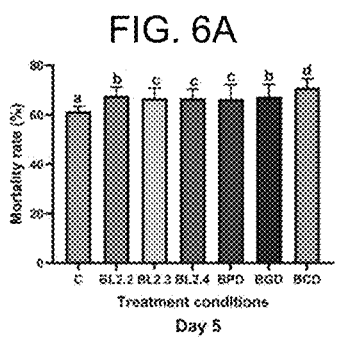
FIG. 6A
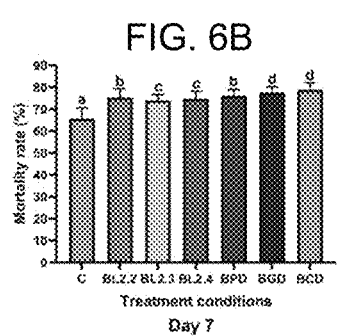
FIG. 6B
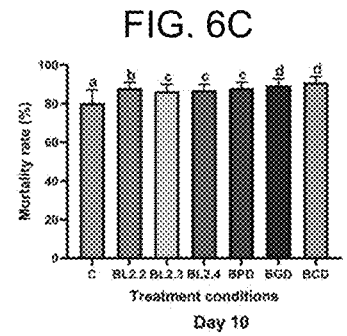
FIG. 6C
42°C
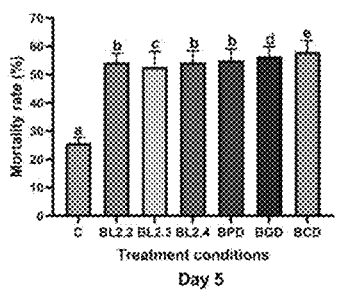
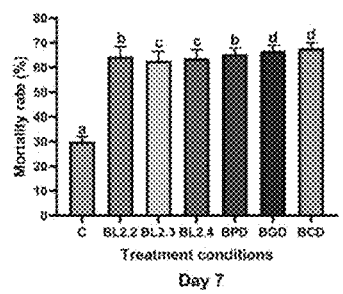
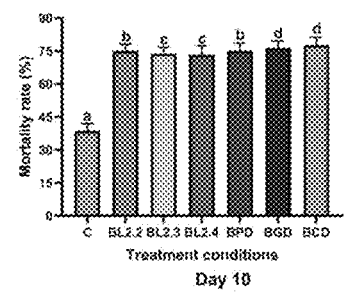
FIG. 6D
FIG. 6E
FIG. 6F

HEAT RESISTANT BIOPESTICIDE AND A METHOD OF PREPARING THE SAME

TECHNICAL FIELD

The invention relates to a field of thermotolerant biopesticide.

BACKGROUND OF THE INVENTION

Pest control in agriculture is challenging, especially in hot environments.

It is common in the desert regions to use chemical pesticides to control pests and diseases in agricultural production. Red palm weevil is a common pest of date palm in the arid regions. The larvae excavate holes in the palm trees and thereby weakening and eventually killing the host plant. It is common in the desert region to use chemical pesticides for killing the red palm weevil. However, in the desert conditions, where the resources are limited, using chemical pesticides are not effective for controlling the Red palm Weevil. Thereby, overusing the chemical pesticides in arid regions to control the Red palm Weevil is not an efficient method and will lead to long-term harmful effect on the entire wildlife, human health, as well as on the environment.

As an alternative to synthetic chemicals, entomopathogenic bacteria, like *Bacillus thuringiensis* with significant action selectivity, offer a promising option. However, *B. thuringiensis* biopesticides face instability due to the natural environmental stresses in arid regions. *B. thuringiensis* is a gram-positive bacterium that forms spores and produces insecticidal crystal proteins (ICPs), δ endotoxin, which is toxic to a range of insect species. It is the highly manufactured microbial insecticide globally, widely used in agriculture due to its non-toxic nature towards humans, livestock, and the environment. Nevertheless, the susceptibility of ICPs to degradation under high temperature, along with ionization by water and other substances, leads to a shortened persistence of biopesticides, particularly in arid regions, which limits its efficacy in controlling pests, reducing its shelf life and application time. This occurs due to the degradation of δ-endotoxin proteins and thus constrains its use as a biopesticide.

There is therefore a need to develop a biopesticide which is heat resistant and is capable of imparting effective removal of the common pests in the arid regions such as the red palm weevil.

SUMMARY OF THE INVENTION

According to one aspect of the invention, there is provided a biopesticide composition comprising a biopesticide; and a late embryogenesis abundant (LEA) protein.

The LEA protein may be elected from any of its eight subgroups: LEA1, LEA2, LEA3, LEA4, LEA5, LEA6, dehydrin and seed maturation protein (SMP). In a preferable embodiment, the LEA protein may be a LEA2/dehydrin protein.

The biopesticide may be in the form of an endotoxin protein.

The endotoxin protein of the invention may preferably be a δ-endotoxin. The δ-endotoxin or delta endotoxin are a family of toxins from the *Bacillus thuringiensis* species of bacteria.

The LEA2/dehydrin protein may be a multi-class family of protein that may be produced in plants in response to abiotic stresses such as drought, cold, salinity stresses, etc. These LEA2/dehydrin proteins may have low molecular weights. The LEA2/dehydrin proteins may further be characterised as being hydrophilic, thermostable and intrinsically disordered. The LEA2/dehydrin protein may be in the form of a recombinant The LEA2/dehydrin protein.

In a preferred embodiment, the endotoxin protein and the LEA2/dehydrin protein may be present in the biopesticide composition in the ratio of about 1:40 (endotoxin:LEA2/dehydrin proteins).

The LEA2/dehydrin protein may be thermostable in nature. The inventors believe that the addition of the LEA2/dehydrin proteins enhances the thermotolerance and stability of biopesticide of the invention. In the biopesticide composition of the invention, the inventors believe that the LEA2/dehydrin proteins confers heat resistance to the endotoxin up to a temperature of about 42° C.

The inventors believe that the advantages of the biopesticide composition of the invention include:
  a) Enhanced efficiency—The integration of LEA2/dehydrin proteins into biopesticides provides an effective solution to enhance the thermotolerance of the biopesticide while retaining its stability, leading to increased efficacy in pest management, especially under temperature stress conditions. This is particularly true while using the biopesticide in the arid regions wherein the average temperature may be about 40° C. or more.
  b) Sustainability—The use of biopesticides is considered more environmentally friendly compared to traditional chemical pesticides. The invention, by improving the stability of biopesticides, contributes to sustainable agricultural practices.
  c) Eco-friendly—The use of biopesticide reduces the reliance on chemical pesticides and promote eco-friendly pest management solutions.
  d) Innovation—The unique combination of plant proteins as a stabilizing mechanism represents a novel approach in the field of pest management.
  e) Farmers and those involved in agricultural practices stand to benefit from the increased efficacy of biopesticides, especially in regions with varying and extreme temperature conditions such as arid conditions.

According to another aspect of the invention, there is provided a method of manufacturing a heat resistant biopesticide composition, the method may comprise providing a biopesticide composition; providing a late embryogenesis abundant (LEA) protein; and combining the LEA protein with the biopesticide composition. The LEA protein may be elected from any of its eight subgroups: LEA1, LEA2, LEA3, LEA4, LEA5, LEA6, dehydrin and seed maturation protein (SMP). In a preferable embodiment, the LEA protein may be a LEA2 protein. The LEA2/dehydrin protein may be in the form of a recombinant The LEA2/dehydrin protein.

The biopesticide composition may comprise an endotoxin.

According to the invention, the recombinant LEA2/dehydrin protein may be prepared by isolating the genes involved for the synthesis of the LEA2/dehydrin protein from a plant. Thereafter, the isolated gene for the dehydrin protein may be expressed in an expression vector.

Preferably, the plant may belong to the xerophytic species. As the xerophytic plants are found in arid regions, they may already experience heat stress and therefore may highly express the LEA2/dehydrin protein.

The expression vector may be a plasmid which is used to introduce a specific gene in a target cell. Upon integration of the plasmid with the LEA2/dehydrin gene sequence, the target cell may be able to express the gene, in other words, manufacture the protein expressed by the specific gene i.e. the recombinant LEA2/dehydrin protein. In this case, the isolated gene for the dehydrin protein may be expressed in a pET-28a vector.

pET-28a vector may be a bacterial expression vector. Any of the bacterial species may be used for the purpose of expression. In a preferred embodiment, the bacteria may be *Escherichia coli* or *E. coli*.

The expressed recombinant LEA2/dehydrin protein may be purified and may be used for mixing with the endotoxin protein.

In a preferred embodiment, the dehydrin protein (or the recombinant protein) may be mixed with the endotoxin protein in a ratio of about 1:40 (endotoxin:LEA2/dehydrin proteins).

In another preferred embodiment, endotoxin protein used in the method of the invention may be a δ-endotoxin. In another preferred embodiment, the dehydrin protein used in the method of the invention may be a late embryogenesis abundant (LEA) protein. Although any of the LEA proteins indicated above may be used, in a preferred embodiment, the LEA protein used in the method of the invention may be a LEA2/dehydrin protein or a recombinant LEA2/dehydrin protein.

The LEA2/dehydrin proteins may provide a stabilizing mechanism, ensuring the sustained efficacy of the endotoxin, under varying temperature conditions. The inventors believe that the invention's non-obvious nature may lie in its ability to harness the protective attributes of plant proteins, adapting them for application in biopesticides to provide a novel and inventive solution to a long-standing issue in agricultural pest management.

BRIEF DESCRIPTION OF THE DRAWINGS

Further features of the invention are described hereinafter by way of a non-limiting example of the invention, with reference to and as illustrated in the accompanying schematic drawings. In the drawings:

FIG. 2 illustrates a schematic diagram of a method of preparing the biopesticide composition of the invention; IDC-A1 Sub AMD FIG. 3A-3F illustrates the 3D structure of the recombinant LEA2/dehydrin protein—*Phoenix dactylifera* LEA2/dehydrin proteins—PdLEA2.2 (FIG. 3A) (Accession number—WCF34208.1), PdLEA2.3 (FIG. 3B) (Accession number—WCF34211.1), and PdLEA2.4 (FIG. 3C) (Accession number—WCF34209.1); *P. dactylifera* dehydrin—PdDHN (FIG. 3D) (Accession number—XP_088798225.1), *Prosopis cineraria* dehydrin—PcDHN (FIG. 3E) (Accession number—XP_054778962.1), and *Citrullus colocynthis* dehydrin—CcDHN (FIG. 3F) (Accession number—XJP22786.1);

FIG. 6A to 6F illustrates the effect of biopesticide composition of the invention on RPW adult mortality rate.

DETAILED DESCRIPTION OF THE INVENTION

To counteract adverse environmental conditions in nature, plants have evolved to produce protein molecules known as LEA Proteins. LEA Proteins comprise short hydrophilic polypeptides which play a role in safeguarding and supporting plant metabolism during stressful conditions, such as, for example, low water availability, high and low temperatures, salinity, and osmotic as well as other stresses. LEA protein include eight subgroups: LEA1, LEA2, LEA3, LEA4, LEA5, LEA6, dehydrin and seed maturation protein (SMP).

According to one aspect of the invention, the invention relates to a biopesticide composition comprising a biopesticide in the form of an endotoxin protein and a late embryogenesis abundant (LEA) protein in the form of a LEA2/dehydrin protein.

More specifically, the invention involves the unique integration of LEA2/dehydrin protein in biopesticide compositions.

Dehydrin Protein (Dehydrin/LEA 2 Proteins)

LEA2 proteins are the prevalent group of LEA proteins and are produced in plants in response to stress. Among the LEA2 proteins, dehydrins constitute a distinct biochemical group, which is generally produced in response to environmental stress conditions such as drought, cold, salinity, chemical stresses, and during a plants development stages such as seed and pollen maturation.

The dehydrins are of low molecular weight compounds and are highly disorganised. Due to the intrinsically disordered structure, LEA2/dehydrin protein takes the structure of another protein molecules and protects them from degradation (chaperone property). A similar role is performed by LEA2/dehydrin proteins in plants under abiotic stress conditions.

Although the LEA2/dehydrin proteins may be obtained from plants undergoing stress, it is very difficult to retrieve such compounds from the plants in high quantity. Further, to retrieve such compounds from plants, the plant materials need to be grinded to extract the dehydrin molecules. For extracting large amounts of dehydrin from plants, a huge amount of plant materials would need to be grinded.

For the purpose of the invention, although a naturally available dehydrin may be extracted from the plant, it is more environmentally friendly, and commercially applicable to prepare the dehydrin protein using recombinant DNA techniques.

In accordance with the invention, recombinant LEA2/dehydrin proteins are from *Phoenix dactylifera* (*P. dactylifera*), *Prosopis cineraria* (*P. cineraria*) and *Citrullus colocynthis* (*C. colocynthis*). The LEA2/dehydrin protein from *P. dactylifera* comprises PdLEA2.2, PdLEA2.3, PdLEA2.4, PdDHN1, the dehydrin protein from *P. cineraria* comprises PcDHN, the dehydrin protein from *C. colocynthis* includes CcDHN.

Figure 1:
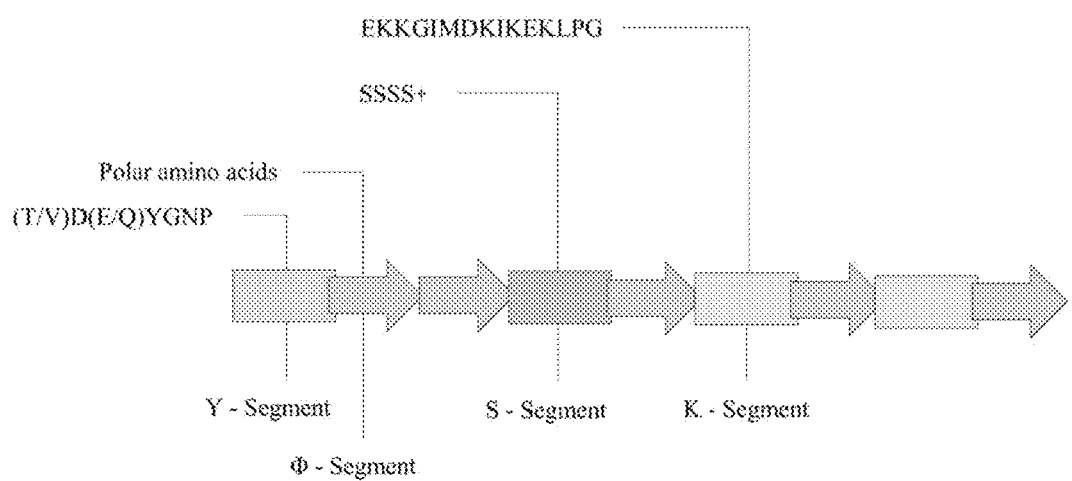
FIG. 1 shows a schematic diagram of a linear chain depicting the YSKn type LEA2 protein (Seq. ID No. 1)

An exemplary structure of the recombinant dehydrin protein is shown in FIG. 1. FIG. 1 shows a linear chain depicting a YSKn type LEA2/dehydrin protein, where different segments in the sequence are represented by their respective letters: Y-Segment: [T/V]D[E/Q]YGNP, φ-Segment: Polar amino acids, S-Segment: Serine track, and K-Segment: EKKGIMDKIKEKLPG. This sequence illustrates the specific arrangement of amino acids within each segment of the YSKn type LEA2/dehydrin proteins, providing a visual representation of the molecular structure.

Method of Manufacturing and Purification of the Dehydrin Protein

FIG. 2 discusses an embodiment for manufacturing of recombinant LEA2/dehydrin proteins. The first step in the manufacturing of the recombinant LEA2/dehydrin protein is identifying and isolating the LEA2/dehydrin genes. Upon identifying the relevant genes, the open reading frames (ORFs) of LEA2/dehydrin proteins were cloned in frame with the polyhistidine tag of the pET-28a expression vector. Recombinant LEA2/dehydrin proteins were expressed in *E. coli* cells (BL21 strain) and evaluated using SDS-PAGE. Following induction with Isopropyl β-d-1-thiogalactopyranoside (IPTG), large quantities of LEA2/dehydrin proteins accumulated in *E. coli* cells.

Affinity chromatography with a nickel column was employed to purify the overexpressed LEA2/dehydrin proteins. The purity of these proteins was confirmed through Western blot analysis utilizing an anti-His6 antibody. The immunoblot revealed bands corresponding to LEA2/dehydrin proteins but not in the control, affirming the presence of purified LEA2/dehydrin proteins.

Isolation and Physicochemical Analysis of LEA2/Dehydrin Proteins

The PdLEA2 proteins are predicted to have molecular weights of 27.88 kDa for PdLEA2.2, 35.43 kDa for PdLEA2.3, and 24.73 kDa for PdLEA2.4.

The dehydrin isolated from date palm, *Prosopis cineraria* (Ghaf tree), and *Citrullus colocynthis* (desert squash), exhibited a conserved amino acid K-segment sequence (EKKGIMDKIKEKLPG) present in them. The molecular weights of PdDHN, CcDHN, and PcDHN were 24.83 kDa, 18.47 kDa, and 23.17 kDa, respectively. Analysis of physicochemical properties indicated that most isolated PdLEA2 proteins had relatively high isoelectric points. The aliphatic index of the LEA2/dehydrin proteins was remarkably high, ranging between 27.95 to 96.81, suggesting that LEA2/dehydrin proteins exhibit thermostability across a broad temperature range.

Disorder Structural Characteristics of LEA2/Dehydrin Proteins

Recombinant LEA2/dehydrin proteins were produced and purified, and their presence was confirmed with motif analysis.

FIG. 3A-3F illustrates the 3D structure of the recombinant LEA2/dehydrin protein—*P. dactylifera* LEA2 proteins—PdLEA2.2 (FIG. 3A), PdLEA2.3 (FIG. 3B), and PdLEA2.4 (FIG. 3C); *P. dactylifera* dehydrin—PdDHN (FIG. 3D), *P. cineraria* dehydrin—PcDHN (FIG. 3E), and *C. colocynthis* dehydrin—CcDHN (FIG. 3F).

The structural analysis of the isolated LEA2/dehydrin proteins exhibited characteristics of intrinsically disordered proteins (IDPs). Three-dimensional structural assessments of the LEA2/dehydrin proteins revealed a disordered segment at the N-terminal region. Subsequent to this segment, an α-helix was identified, and the tertiary structure comprised three β-hairpins and β-strands. As a result, the prevailing folded secondary structure within the LEA2/dehydrin protein sequences were the β-strand, interspersed with random coils.

The impact of the dehydrin protein on the efficacy of endotoxin against the devastating date palm pest, the Red palm Weevil was studied through bioassays, assessing egg hatching inhibition, larval, and adult insect mortality rate under normal and heat stress conditions, which are provided below.

RPW Samples

RPW larvae and RPW adult insects were collected from infested and untreated trees and baited pheromone traps from the date palm fields of Al Ain City. The collected samples were transported in plastic containers with palm tissues as a food supply in transit. Adults and larvae were further fed on sugarcane plant pieces in plastic tissue culture bottles in the laboratory and adults were allowed to oviposit eggs.

Preparing the Biopesticide Composition

A 500-ppm solution of the endotoxin concentrate was prepared in a total volume of 300 ml using distilled water. A buffer containing LEA2/dehydrin proteins or water was added to the endotoxin solution at a mass ratio of 1:40 (endotoxin:LEA2/dehydrin proteins) as an additive.

It is to be understood that the endotoxin can be substituted with the solution of *Bacillus thuringiensis* var. *tenebrionis*. This *bacillus* species is available in different forms. One example is Novodor-FC.

Different biopesticide solutions of the invention were be prepared using different LEA proteins obtained from *P. dactylifera* LEA2 proteins—using PdLEA2.2—BL2.2, using PdLEA2.3—BL2.3, and using PdLEA2.4 BL2.4; *P. dactylifera* dehydrin—using PdDHN—BPD, *P. cineraria* dehydrin—using PcDHN—BGD, and *C. colocynthis* dehydrin—using CcDHN—BCD Assay In one embodiment of the invention, the biopesticide composition of the invention prepared was applied to sugarcane leaf samples. The biopesticide may be applied by any of the techniques known in the art. The most common technique being spraying the biopesticide composition on the leaves. The leaves were air-dried overnight at room temperature.

Assay with RPW Eggs

Newly produced eggs were placed in a petri dish (90 mm Ø) with a layer of cotton on the bottom, then sprayed with 10 ml of the prepared solutions. The solutions include the control solution with only endotoxin and the biopesticide composition of the invention. The inoculated petri dish was incubated at room temperature (25±2° C.) and under heat stress condition of 42±2° C. with a relative humidity of 65%.

The number of hatching larvae was recorded daily until the seventh day post treatment. The eggs that remained unhatched after the seventh day were considered nonviable.

Assay with RPW Larvae and RPW Adult

For larvae and adults, sugarcane pieces were sprayed with the biopesticide composition of the invention with or without LEA2/dehydrin proteins. The samples, including treated and untreated controls, were divided into three replicates and placed in insect culture plates, with separate plates for RPW larvae and RPW adult. The plates were exposed to two temperature conditions, room temperature, 25±2° C., and a heat stress condition of 42±2° C. with 65% relative humidity. Mortality rates were recorded for 5 days, 7 days and 10 days post-treatments.

Figure 4A:
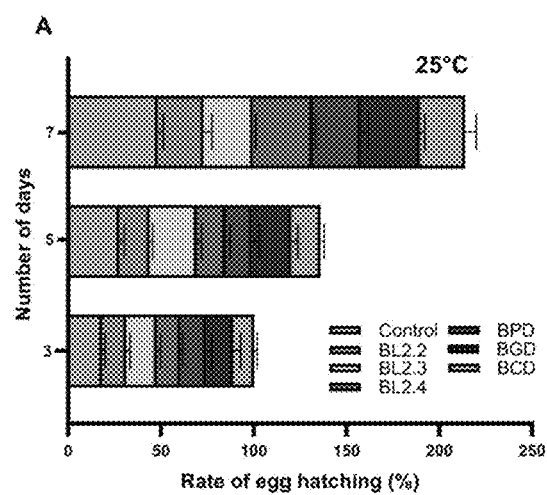
FIG. 4A illustrates the endotoxin effect on RPW egg hatching under normal temperature condition and FIG. 4B illustrates the endotoxin effect on RPW egg hatching under heat stress condition.
Figure 4B:
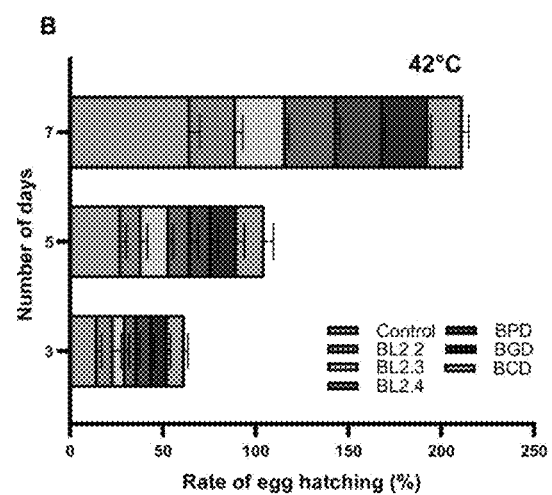

FIG. 4A illustrates the endotoxin effect on RPW egg hatching under normal temperature condition and FIG. 4B illustrates the endotoxin effect on RPW egg hatching under heat stress condition.

From FIGS. 4A and 4B, it is noted that there is a significant difference in the egg hatching rate of RPW eggs between only the endotoxin application with and without LEA2/dehydrin proteins at both the control temperature of 25° C. and the elevated temperature of 42° C.

Under control temperature conditions, the average egg hatching rate exhibited a slight variation between the control and endotoxin with the addition of LEA2/dehydrin proteins (FIG. 4A). As shown in FIG. 4A, all endotoxin solutions complemented with LEA2/dehydrin proteins showed lower than average egg hatching rates compared to the control. This suggests that the effectiveness of the endotoxin solution was improved by the inclusion of LEA2/dehydrin proteins, preventing the hatching of RPW eggs. After day 7 at the control temperature, the endotoxin solution with CcDHN recorded the lowest egg hatching rate at 24.3%, contrasting with the highest hatching rate observed without LEA2/dehydrin proteins at 48.3%.

Data are expressed as the means±SD (n=3), analyzed using one-way ANOVA. Under the heat stress condition of 42° C., significant differences were observed in the hatching rate of RPW eggs over the 7-day period. The addition of LEA2/dehydrin proteins was found to reduce the egg hatching of RPW under the heat stress condition. Specifically, during the third day, the endotoxin solution with PdLEA2.2 proteins exhibited an egg hatching rate of 8.6%, PdLEA2.3 had a rate of 6.3%, PdLEA2.4 proteins showed 6.3%, PdDHN had 8.3%, and CcDHN had 9.3%, respectively. In contrast, the control endotoxin had a hatching rate of 15%. On day 5, the hatching rate for PdLEA2.2 was 11%, PdLEA2.3 had 15%, PdLEA2.4 showed 11.3%, PdDHN displayed 11.3.%, PcDHN had 13.6%, and CcDHN had 15%, whereas for the endotoxin solution without PdLEA2 proteins, the hatching rate of 27.6% was observed. The highest egg hatching rate, 18.6%, was observed for the endotoxin solution without LEA2/dehydrin proteins, while the lowest hatching was for endotoxin with CcDHN at 34.7% on day 7 was observed. This indicates that the presence of LEA2/dehydrin proteins prevented the degradation of endotoxin in the biopesticide composition, thereby inhibiting the hatching of RPW eggs under heat stress.

It concludes that LEA2/dehydrin proteins protect the endotoxin toxicity under control temperature of 25° C. and heat stress of 42° C. on RPW eggs hatching.

FIG. 5A-5F illustrates the effect of the biopesticide composition of the invention on RPW larval mortality rate.

Figure 5A:
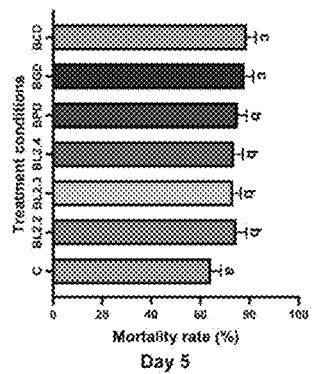
FIG. 5A-5F illustrates the effect of the biopesticide composition of the invention on RPW larval mortality rate.
Figure 5B:
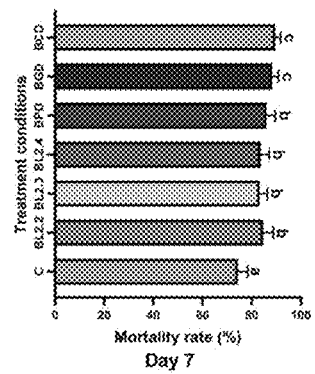
Figure 5C:
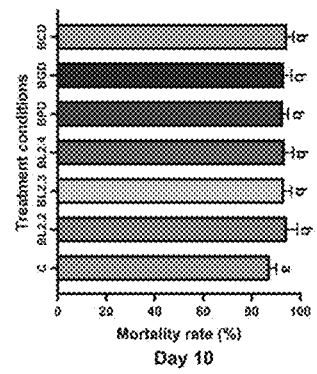

The impact of adding PdLEA2.2, PdLEA2.3, PdLEA2.4, PdDHN, PcDHN, and CcDHN proteins to the endotoxin solution's effect on larvae was compared to the control endotoxin solution without LEA2/dehydrin proteins under normal conditions at 25° C. (FIGS. 5A-5C). On the fifth day of treatment, endotoxin toxicity was slightly lower in the absence of LEA2/dehydrin proteins, while CcDHN caused 79% larval mortality. After 7 days of endotoxin treatment at normal temperature, the addition of PdLEA2.2, PdLEA2.3, PdLEA2.4, PdDHN, PcDHN, and CcDHN proteins to the endotoxin resulted in mortalities of 84.7%, 83.3%, 83.6%, 86%, 88.3%, and 89.6%, respectively (FIG. 5B). Following 10 days of treatment, mortality rates of 87.6%, 94.4%, 93.7%, 93%, 93.3%, and 94.6% were observed for larvae in the endotoxin solution with PdLEA2.2, PdLEA2.3, PdLEA2.4, PdDHN, PcDHN, and CcDHN, respectively (FIG. 5C).

Figure 5D:
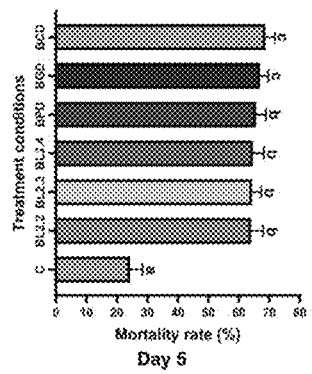
Figure 5E:
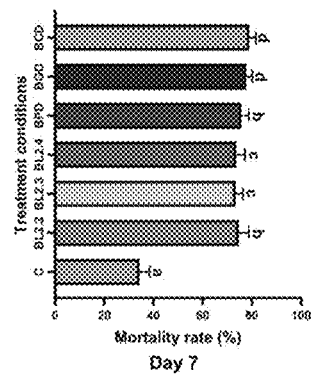
Figure 5F:
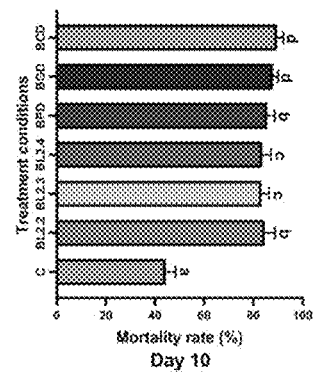

A highly significant difference in larval mortality rates was observed under the heat stress condition with endotoxin application at 42° C. (FIG. 5D-5F). On the fifth day, the mortality rate for the control endotoxin was 24.3%, but it increased to 68.6% with the addition of PcDHN proteins to the endotoxin solution (FIG. 5D). A similar trend was observed on day 7 (FIG. 5E). Moreover, after 10 days of heat stress and treatments, the mortality rate in the absence of LEA2/dehydrin proteins was 44.2%, whereas in the presence of PdLEA2.2, PdLEA2.3, PdLEA2.4, PdDHNA, PcDHN, and CcDHN, it was 84.7%, 83.3%, 83.6%, 85.6%, 88%, and 89.7%, respectively (FIG. 5F). This indicates that LEA2/DHN proteins have a preservative effect on endotoxin under heat stress, enhancing the toxicity of the biopesticide composition of the invention against RPW larvae at higher temperatures compared to using endotoxin solution alone.

FIG. 6A to 6F illustrates the effect of biopesticide composition of the invention on RPW adult mortality rate.

To assess the protective effect of LEA2/dehydrin proteins on endotoxin solution and their impact on the mortality of RPW adults under normal temperature and heat stress conditions at 42° C., recombinant PdLEA2.2, PdLEA2.3, PdLEA2.4, PdDHN, PcDHN, and CcDHN proteins were added into the endotoxin solutions (FIG. 6A-6E). Treatments were conducted with and without LEA2/dehydrin proteins over 15-day intervals, and mortality rates were measured during 5 day, 7 day, and 10 day periods. A slight but statistically significant difference ($p<0.05$) was observed in the mortality rate of RPW adults with and without LEA2/dehydrin proteins at different time intervals under normal temperature conditions. The CcDHN protein complemented endotoxin solution exhibited the highest percentage of mortality, reaching 71% on day 5, 79% on day 7, and 91% on day 10 under normal temperature conditions (FIGS. 6A, 6B, 6C). In contrast, the endotoxin solution without LEA2/dehydrin proteins recorded the lowest mortality rates for adult RPW, with 61.3% on day 5, 65.6% on day 7, and 80.3% on day 10, respectively (FIGS. 6A, 6B, 6C). A highly significant difference ($p<0.001$) was observed for the 10-day time interval of endotoxin treatments with and without LEA2/dehydrin proteins under heat stress (FIG. 6D). On the fifth day of heat stress, the highest mortality rate of RPW was observed for endotoxin with CcDHN at 58%, and the lowest was for the control without PdLEA2 proteins at 25.8%. Similarly, on day 7, PdLEA2.2, PdLEA2.3, PdLEA2.4, PdDHN, PcDHN, and CcDHN increased the mortality of RPW adults to 64.3%, 62.6%, 63.6%, 65.3%, 66.7%, and 67.6%, respectively (FIG. 6E). In contrast, endotoxin without LEA2/dehydrin proteins exhibited only 30% mortality. After the 10-day treatment at 42° C., PdLEA2.2 added to the endotoxin solution resulted in a mortality rate of 75% for adult RPW, while PdLEA2.3, PdLEA2.4, PdDHN, PcDHN, and CcDHN led to mortality rates of 73.6%, 73.3%, 75%, 76.3%, and 77.6%, respectively (FIG. 6F). In comparison, the mortality of RPW adults was 38.3% without PdLEA2 proteins added to the endotoxin solution under heat stress. This suggests that LEA2/dehydrin proteins contribute to the stabilization of endotoxin under heat stress conditions.

Characteristics of LEA2/dehydrin protein making them an ideal choice for use with the endotoxin in the biopesticide composition of the invention includes but is not limited to:

LEA2/dehydrin proteins acts as chaperones and take up the structure of endotoxin protein under heat stress conditions;

Dehydrin protein (LEA2) protects the toxicity of the endotoxin under high temperatures;

Dehydrin protein (LEA2) enhances the endotoxin toxicity and maintains it if not increasing the mortality of the pest Red palm Weevil larva at high temperatures;

Dehydrin protein reduces the aggregation of endotoxin under normal and high temperature condition; and Dehydrin protein (LEA2) further increases the shelf life of the biopesticide composition of the invention.

The invention described herein is susceptible to variations, modifications, and/or additions other than those specifically described, and it is to be understood that the invention includes all such variations, modifications and/or additions which fall within the scope of the following claims.

The inventors envisage that other LEA proteins, other than those described and exemplified above may be used in a method of manufacturing a heat resistant biopesticide composition. Similarly, the inventors envisage that other LEA proteins, other than those described and exemplified above may be used in a biopesticide composition.

The inventors envisage that other biopesticides, other than those described and exemplified above may be used in a method of manufacturing a heat resistant biopesticide composition. Similarly, the inventors envisage that other biopesticides, other than those described and exemplified above may be used in a biopesticide composition.

The invention claimed is:

1. A biopesticide composition comprising a biopesticide and a late embryogenesis abundant (LEA) protein, wherein the LEA protein is a recombinant LEA2 protein, and wherein the biopesticide and the recombinant LEA2 protein are present in the ratio of about 1:40 (biopesticide:LEA2 protein).

2. The biopesticide composition as claimed in claim 1, wherein the biopesticide is in the form of an endotoxin protein.

3. The biopesticide composition as claimed in claim 2, wherein the endotoxin protein is a δ-endotoxin.

4. The biopesticide composition as claimed in claim 1, wherein the biopesticide composition is resistant to heat up to about 42° C.

5. A method of manufacturing a heat resistant biopesticide composition comprising:
   providing a biopesticide,
   providing a late embryogenesis abundant (LEA) protein, wherein the LEA protein is a recombinant LEA2 protein, and
   combining the biopesticide and the recombination LEA2 protein, wherein the biopesticide and the recombinant LEA2 protein are present in the ratio of about 1:40 (biopesticide:LEA2 protein).

6. The method as claimed in claim 5, wherein providing the LEA protein comprises isolating genes for a LEA protein from a plant and expressing the isolated gene for the LEA protein in an expression vector to produce a recombinant LEA2 protein.

7. The method as claimed in claim 6, wherein the expression vector is a pET-28a vector.

8. The method as claimed in claim 6, wherein the method further comprises purification of the recombinant LEA2 protein.

9. The method as claimed in claim 5, wherein the biopesticide is in the form of endotoxin protein.

10. The method as claimed in claim 9, wherein the endotoxin protein is an δ-endotoxin.

* * * * *

```
                            SEQUENCE LISTING

Sequence total quantity: 7
SEQ ID NO: 1            moltype = AA  length = 28
FEATURE                 Location/Qualifiers
REGION                  1..28
                        note = YSKn type LEA2 protein
source                  1..28
                        mol_type = protein
                        organism = unidentified
SEQUENCE: 1
TVDEQYGNPS SSSEKKGIMD KIKEKLPG                                         28

SEQ ID NO: 2            moltype = AA  length = 251
FEATURE                 Location/Qualifiers
REGION                  1..251
                        note = PdLEA2.2 (Accession number- WCF34208.1)
source                  1..251
                        mol_type = protein
                        organism = Phoenix dactylifera
SEQUENCE: 2
MAEQQRIHPV DVEAPSQAAP LVPPELSRSD KGDPAVAGQY PHHRRTIPVA HSRPPKRRRS        60
CCCKCLCWTI LTIIILIVLV AATLGILYLI FDPKLPKYSV DRLRVSTFSV DNNLTAHAGF       120
DVTVTAENPN KKIGIYYEGG SHLSVWYSGF SLCEGEPPEF YQGHRNTTVL TVVLTGEAQL       180
GSTEMTALQQ QQQTGMVPLN FKGDVPVRVK LGSLKLWKVT SRVRCSLVVD SLTANNQIQI       240
RSSSCKFRLK L                                                           251

SEQ ID NO: 3            moltype = AA  length = 317
FEATURE                 Location/Qualifiers
REGION                  1..317
                        note = PdLEA2.3 (Accession number- WCF34211.1)
source                  1..317
                        mol_type = protein
                        organism = Phoenix dactylifera
SEQUENCE: 3
MASFDKPEVV EREVKDKEHR EEDKHEEKGG FIEKVKDFIH DIGEKIEGAI GFGKPTADVA        60
GVHIPSINLE KAEIVVDVLI TNPNPVPIPL IDIDYLIESD GRKLVSGLIP DAGTIHAHGS       120
ETVKIPVTLI YDDIKNTYDD IKPGSIIPYR IKVDLIVDVP IFGRLTLPLE KKGEIPVPYK       180
PDVDLEKIHF NKFSFEETTA TLHLKLENKN DFDLGLNALD YEIWLSDVSI GAAELTKSIK       240
LEKNGITKME IPITFRPKDF GSALWDMIRG RGTGYSLKGN IDVDTPFGRM KLPICKEGGT       300
TRLKKQDDDD DDDDEVC                                                     317

SEQ ID NO: 4            moltype = AA  length = 216
FEATURE                 Location/Qualifiers
REGION                  1..216
                        note = PdLEA2.4 (Accession number - WCF34209.1)
source                  1..216
                        mol_type = protein
                        organism = Phoenix dactylifera
SEQUENCE: 4
MGRTYYGAPI PPEQHYEQRH RSCYCCLLST LIKTIIAFCL ALGITLLVLW LVFRPSKVEV        60
SVEKASLTSF NLTTSPTNLY YNLSADISIR NPNKRIGICY DWLEADPYYQ GHRFDWEALP       120
SFYQGHKNTT MLYPVLKGNS AIGLGDSDIE EFKKENETSF FNVDIWLIGQ VRYKFGSVTT       180
RRYTMRVKCE LGLPLAAHRT SGASSFTRTE CDVVDY                                216

SEQ ID NO: 5            moltype = AA  length = 225
FEATURE                 Location/Qualifiers
REGION                  1..225
                        note = PdDHN (Accession number - XP_008798225.1)
source                  1..225
                        mol_type = protein
                        organism = Phoenix dactylifera
SEQUENCE: 5
MAEEQKQEVE VKDRGLFDFM GRKKEEEQEV LVAGVEKVHI EEGKKEEKEE EKKESLLEKL        60
HRSHSSSSSS SSEEEGGEGE NKEKKKKKKK KGLVEKIKGK IGGEEEEKPA VVEQEVAIAA      120
VSSESEDSTV KVEVVDESLK VEGVPEEEKK GFLEKIKEKL PGHHKKPEEA AAPAAECAGQ       180
GTKEHETDHG HEGKEKKGIL GKLMEKLPGY HKNGGEESEK AGATH                       225

SEQ ID NO: 6            moltype = AA  length = 223
FEATURE                 Location/Qualifiers
REGION                  1..223
                        note = PcDHN (Accession number - XP_054778962.1)
source                  1..223
                        mol_type = protein
```

-continued

```
                organism = Prosopis cineraria
SEQUENCE: 6
MAEAQLRDER GNPIQLTDQY GNPVKLTDEH GNPVHLAGVA TTVPAAGSHY GSQGTGTTGF    60
GTHGGVTGTN TSGFGTYGTG TYGGGATRGT GIGGGTTVGD LMSDHTKQHH TGELRRSNSS   120
SSSSSEDDGE GGRRKKKGWK EKIKEKLPGG GGGGEAINYP QNQGHVKTTT TDTYTTTMAT   180
GHGQLPTGAG GVKHHDTGHE HHEHHEKKSI MEKIRDKLPG AHH                    223

SEQ ID NO: 7            moltype = AA  length = 170
FEATURE                 Location/Qualifiers
REGION                  1..170
                        note = CcDHN (Accession number - XJP22786.1)
source                  1..170
                        mol_type = protein
                        organism = Citrullus colocynthis
SEQUENCE: 7
MAHYQSGTDQ YGNPIRQTDE YGNVISETAQ YGDPLRRTGE FRETDQYGNP VRQTGEYGNP    60
IGTGTGGTYE TGGYGGTGYG GGHHQQHKEH GGILHRSGSS SSSSSEDDGH GGRRKKGLKE   120
KIKEKLPGHH ETPGGYSTTT PGGYSSAEYG GQHEKKGIME KIKEKLPGHH              170
```